(12) United States Patent
Chefitz

(10) Patent No.: US 12,702,304 B2
(45) Date of Patent: Aug. 11, 2026

(54) INTRAOPERATIVE PROBE FOR CANCER DIAGNOSIS AND TREATMENT

(71) Applicant: 123IV, Inc., New Rochelle, NY (US)

(72) Inventor: Allen B. Chefitz, New Rochelle, NY (US)

(73) Assignee: 123IV, Inc., New Rochelle, NY (US)

( * ) Notice: Subject to any disclaimer, the term of this patent is extended or adjusted under 35 U.S.C. 154(b) by 0 days.

(21) Appl. No.: 19/343,090

(22) Filed: Sep. 29, 2025

(65) Prior Publication Data

US 2026/0174336 A1 Jun. 25, 2026

Related U.S. Application Data

(60) Provisional application No. 63/700,861, filed on Sep. 30, 2024.

(51) Int. Cl.
*A61B 5/00* (2006.01)

(52) U.S. Cl.
CPC .......... *A61B 5/0077* (2013.01); *A61B 5/0075* (2013.01); *A61B 5/0084* (2013.01)

(58) Field of Classification Search
CPC ... A61B 5/0077; A61B 5/0075; A61B 5/0084; A61B 5/00
See application file for complete search history.

(56) References Cited

U.S. PATENT DOCUMENTS

| | | | | |
|---|---|---|---|---|
| 5,606,971 | A | 3/1997 | Sarvazyan | |
| 2015/0366527 | A1 | 12/2015 | Yu et al. | |
| 2016/0000329 | A1* | 1/2016 | Kircher ................ | A61B 5/0084 600/431 |
| 2017/0020460 | A1 | 1/2017 | Leblond et al. | |

OTHER PUBLICATIONS

PCT/US2025/048688, International Search Report and Written Opinion, Jan. 29, 2026.
Dirrichs, et al., "Shear Wave Elastography (SWE) for Monitoring of Treatment of Tendinopathies: A double-blinded, longitudinal clinical ctudy," Abstract, from Academic Radiology, 2018, vol. 25, No. 3.

* cited by examiner

*Primary Examiner* — Carl H Layno
*Assistant Examiner* — Aya Ziad Bakkar
(74) *Attorney, Agent, or Firm* — David H. Judson

(57) ABSTRACT

An intraoperative probe combines Raman spectroscopy, shear wave elastography (SWE), and photodynamic therapy (PDT), preferably in a single hand-held device with real-time machine learning analysis. The machine learning independently analyzes and then fuses the data from different modalities for real-time cancer diagnostic predictions. The approach herein leverages simultaneous (or near-simultaneous) collection and real-time processing of Raman and SWE data for immediate cancer diagnostic feedback and therapeutic action. The hand-held device is precisely configured to target the same focal point with three different modalities—Raman, SWE, and PDT—by positioning the modalities within the device into the same location, either with an array of mirrors or an automatic or manual rotation mechanism.

22 Claims, 10 Drawing Sheets

INTRAOPERATIVE PROBE FOR CANCER DIAGNOSIS AND TREATMENT

BACKGROUND

Recurrent cancer after undergoing cancer surgery continues to be a problem, accounting for repeat surgeries, increased morbidity and mortality. When a surgeon operates on a patient with a solid tumor, they use preoperative imaging and experience to decide which anatomical structures to remove and with how much margin of grossly normal tissue. In cancer surgery, the task of removing all the cancerous tissue can be examined on two different levels-macroscopic and microscopic. Both can present as surgical dilemmas. For example, on a macroscopic level, is the fatty (lipomatous) structure the surgeon is seeing during surgery cancer or not? On a microscopic level, if the surgeon determines, e.g., based on experience and preoperative imaging, that the structure is indeed cancer, how much of the surrounding "normal" tissue needs to be removed to achieve negative microscopic margins? Removing adjacent vital structures, as in vital arteries, with its attendant risks, could be avoided if the surgeon could determine intraoperatively the oncologic status of that adjacent tissue. A separate question is how much of a negative margin is optimal. This last question could be answered with an assurance that the surgery has removed completely negative microscopic margins.

Recent advances in multimodal imaging focus on combining multiple optical spectroscopies, such as multispectral optical and mass spectroscopy modalities for cancer detection, as well as nanoparticles for labels. Unlike other areas of medical diagnostics, such as infection, intraoperative cancer diagnostics requires both a very high sensitivity and specificity. Leaving cancer behind (sensitivity) and removing critical, normal tissue (specificity) are equally problematic. To most accurately apply an intraoperative, in-vivo, real-time probe with diagnostic and therapeutic capabilities, the following factors must be considered. In particular, living tissue is in motion, and the microscopic target in the tissue of interest is not visible to the naked eye. Also, to benefit most from the advantages of employing multiple modalities, the focus of each modality in the device should simultaneously target the identical area in the tissue of interest, thereby maximizing the benefits of each modality.

Combining Raman spectroscopy with other modalities for intravascular plaque identification has been achieved. Likewise, imaging that enhances the Raman signal or adds structural detail has been described. Structural imaging modalities, such as CT, MRI, or standard ultrasound, however, do not provide the key distinguishing physical property and molecular characteristics of cancers from benign tissue, such as microscopic properties, molecular specificity, and subtle soft tissue differences.

SUMMARY

To significantly improve cancer surgery and, in turn, lower morbidity and mortality of surgery, namely, by ensuring complete removal of all cancerous tissue—both macroscopic and microscopic, this disclosure provides for a "search and destroy" intraoperative probe that combines various modalities to examine the same tissue at the same spot in real time simultaneously (or near-simultaneously). In examining the same focus of tissue with multiple modalities in this manner, the precision is greatly improved over current methodologies.

In one embodiment, the intraoperative diagnostic and therapeutic probe is user friendly, hand-held, and preferably all functions are contained within one device. The results are easy to recognize on the device, as is the integrated therapeutic option on the same device. In a variant embodiment, the probe is used in association with a robotic surgical platform.

The probe provides physical characteristics of the tumor to augment what a surgeon would normally obtain with palpation and vision—stiffness (shear wave elasticity) and molecular detail (Raman spectroscopy) without the use of labels.

According to a specific embodiment, the intraoperative probe combines several modalities, namely, Raman spectroscopy in a Raman module/unit, shear wave elastography (SWE) in an SWE module/unit, and a laser ablation module/unit, in a single hand-held or robotic assembly-supported device. The Raman module provides biochemical analysis, the SWE module provides mechanical tissue classification, and the laser ablation unit that, when activated, provides for highly-targeted removal of malignant tissues. As will be described, the Raman, SWE and ablation components are supported in a coaxial arrangement to intraoperatively target a same target point, with the Raman and SWE components used for detection (search), and the ablation unit used for the destroy function. This coaxial arrangement provides significant advantages, in that it enables the single probe to target the same focal point with different modalities (Raman, SWE and ablation), thereby enabling simultaneous (or near-simultaneous) collection and real-time processing of data for real-time (or near real-time) cancer diagnostic feedback and, when necessary, therapeutic action.

According to a further aspect, the multimodal operations are facilitated using control functions that leverage machine learning technologies. In one aspect, the machine learning independently analyzes and then fuses the data from different modalities for real-time cancer diagnostic predictions. In particular, and once the Raman laser and ultrasonic shear wave elasticity inputs are applied to the same tissue focal area, one or more machine learning algorithms, trained and tested with cross-validations, provides an immediate classification visible on a user interface of the device. In this embodiment, the machine learning fuses data from both diagnostic modalities (Raman and SWE) to classify tissue pathology. The device outputs the detection result visibly, audibly and/or using tactile feedback. Once malignancy is detected and indicated, the surgeon then activates the therapeutic function of the probe. Re-scanning of the tissue post-therapy is then carried out to confirm complete removal of disease tissue.

To provide a concrete operating "search and destroy" example, it is known that tumor-specific antigens are often found on the cell surface of cancer cells. After intravenous injection of a fluorescent-antibody conjugate that targets a tumor specific antigen on the surface of the tissue of interest, the tissue of interest becomes visible, although with a low specificity. In this example use case, the probe is then used as follows: (i) the shear wave elastography (SWE) transducer and sensors on the device are activated to receive data regarding the macroscopic nature of the tissue of interest (stiffness or elasticity); (ii) the Raman laser is activated to receive the inelastic Raman spectroscopy data and molecular signature of the same tissue; (iii) the fused results of the machine learning algorithms (late fusion) are displayed; (iv) a fluorescent antibody conjugate is injected, the fluorescent tissue is visualized, and the therapeutic laser is activated to photo-ablate the tissue if concordant with Raman or SWE positivity; and (v) the Raman and SWE acquisition are then repeated to confirm no residual disease.

The foregoing has outlined some of the more pertinent features of the subject matter. These features should be construed to be merely illustrative. Many other beneficial results can be attained by applying the disclosed subject matter in a different manner or by modifying the subject matter as will be described.

DETAILED DESCRIPTION

Figure 1:
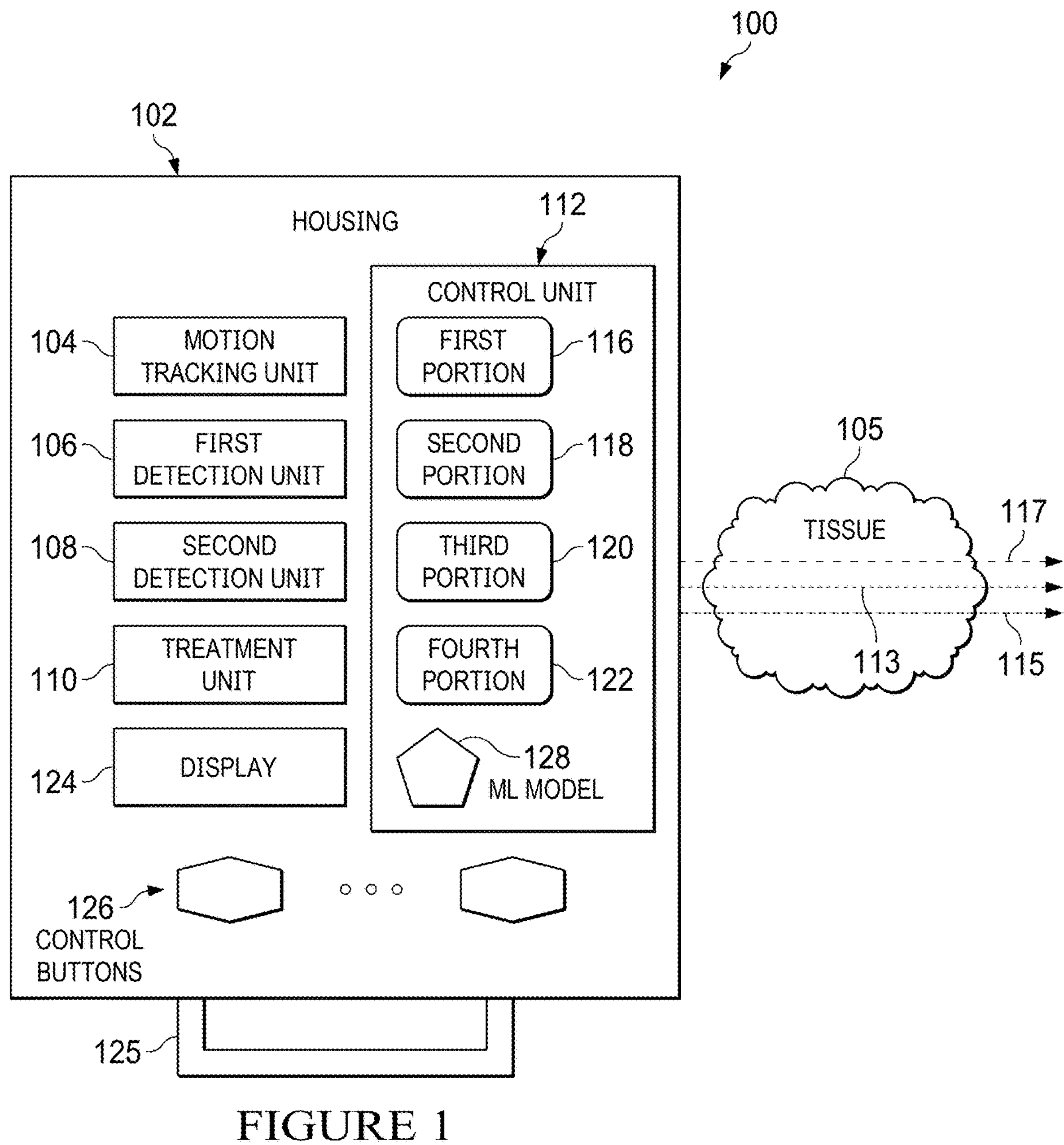
FIG. 1 depicts a block diagram of a multimodal cancer detection and treatment probe according to this disclosure.

FIG. 1 depicts a block diagram of intraoperative surgical probe 100 for detecting and treating cancerous tissue in real-time. The probe comprises a housing 102 that supports a set of components. According to one embodiment, the components include a motion tracking unit 104, a first detection unit 106, a second detection unit 108, a treatment unit 110, and a control unit 112. The motion tracking unit 104 receives one or more inputs, and in response continually generates tracking data representing a displacement of a focal region of tissue 105, together with a predicted motion of the focal region over a given time horizon (e.g., as measured in milliseconds). The first detection unit 106 is controllable by the control unit 112 to output a first output beam along a first axis 113, and in response receive first data. A representative first detection unit is a Shear Wave Elastography (SWE) device, the first axis 113 is an acoustic axis, the output beam is an ultrasound beam, and the first data is data representing stiffness of the focal region of tissue 105. The second detection unit 108 is controllable by the control unit 112 to output a second output beam along a second axis 115, and in response receive second data. A representative second detection unit is a Raman spectrometer, the second axis is an optical axis 115, the second output beam is scattered light, and the second data comprises Raman spectra. The treatment unit 110 is also controllable by the control unit 112 to output a third output beam along a third axis 117. A representative treatment unit is a laser ablation device, such as a cooled pulsed laser, or a picosecond pulsed laser, in which case the third axis 117 is also an optical axis. An attosecond pulsed laser may also be used. The ablation device actively destroys tissue that has been identified as diseased by the control unit 112. To that end, the first, second and third axes are co-aligned so as to selectively converge one or more of the first, second and third output beams on the focal region of tissue 105. This co-alignment is slightly exaggerated in the figure for ease of illustration. The control unit 112 has a first portion 116, a second portion 118, and a third portion 120. A representative control unit 112 comprises one or more hardware processors that execute software comprising a set of control programs as embodied in the first, second and third portions. For example, the first portion 116 is a control program or routine that receives and processes the tracking data to generate one or more output signals indicating that a residual motion of the focal region is less than a threshold. The second portion 118 is a control program or routine that is responsive to a first output signal to activate the second detection unit 108 in association with the first detection unit 106, to receive and analyze the first and the second data, generate respective first and second diagnostic outputs, and based on the first and second diagnostic outputs classify the tissue as normal or diseased. As will be described, this classification typically leverages one or more machine learning (ML) models. The third portion 120 is a control program or routine that is responsive to an indication from the second portion 118 that the tissue is diseased together with receipt of a second output signal from the control unit first portion to arm the treatment unit 110 to enable output of the treatment beam on the focal region of tissue 105 (or some portion thereof). The treatment beam is then activated automatically or by the surgeon to ablate the diseased tissue. Following treatment, the probe is configured to re-scan the tissue to enable the surgeon (or the system operating autonomously) to determine whether there is any residual diseased tissue. To this end, the control unit also includes a fourth portion 122 that is responsive to an activation of the treatment unit 110 together with receipt of a third output signal from the control unit first portion to initiate the re-scan of the focal region of tissue 105, typically using the first and second detection units 106 and 108.

The control unit first, second, third and fourth portions may be implemented as a single set of software. Thus, the notion of a "portion" here is intended to be construed to refer to a control function or operation, typically a software program, process, execution thread or the like, and associated data structures. The probe typically includes an Operating System (OS), such as Linux, and other application programs and utilities. The control unit software is stored in on-board disk storage, and the device further includes sufficient memory (e.g., RAM) into which the control software is loaded for execution by the one or more hardware processors of the control unit. One or more programs and machine learning models (such as described below) may also be stored in read-only memory, programmable memory, and other such known components. Control components may also be implemented using field-programmable gate arrays (FPGA), programmable logic devices (PLDs) or blocks, and others.

Generalizing, the interoperative probe of this disclosure is configured for being held by a surgeon or by a robotic assembly and used during cancer surgery. To this end, and as further depicted in FIG. 1, the probe housing 102 also supports a display 124, and (in the handheld embodiment) an underlying handle 125 by which the surgeon (for example) holds and manipulates the probe. A set of one or more controls 126, e.g., buttons, are supported on the housing or handle to enable the surgeon to manipulate the units/devices that preferably are also supported within the probe in an unitary/integral assembly. In a preferred implementation described in more detail below, all of the optical components and electronics are supported within the probe itself. Typically, the optical components comprise at least two (2) optical paths, namely, a laser projection path, and an optical imaging path. There may be multiple sets of optical paths. Generally, the laser projection path preferably comprises one or more lasers, mirrors, spatial light modulators, lenses and prisms. In this embodiment, which is not intending to be limiting, the optical imaging path comprises a high speed and high resolution CCD (or CMOS) sensor or the like to capture the captured data. In addition, as noted above preferably the optical components comprise a Raman spectroscopy unit. For the shear wave elastography, the shear waves are generated by an ultrasound transducer, which comprises an array of piezoelectric crystals, and emits a high-intensity, focused acoustic pulse into the tissue. The shear wave may be point-based (p-SWE), or 2D-based (2D-SWE). The electronics typically include a microcontroller or microprocessor, and associated storage for the operating system, software, utilities and data (collectively a controller unit). The software typically includes control software, scanning software, detection software, and analysis software. In a representative embodiment as noted above, the hand-held intraoperative probe comprises the following components: an ultrasound shear wave elastography (SWE) transducer unit, a Raman problem, a laser fiber for the ablation unit, and a display. The information provided on the display may vary. In a typical use case, and following detection of relevant data with respect to tissue of interest, the display indicates at least a probability of benign or malignant, together with a confidence level indication. The laser for the ablation unit may be the same laser as used for the Raman unit, with an adjustment mode on the device for power and wavelength, or distinct lasers (in the same or distinct optical paths) may be used for the Raman and laser ablation components.

While laser ablation to destroy tissue determined to be diseased, this is not a limitation. The treatment unit may instead comprise a photodynamic therapy (PDT) subsystem configured to illuminate and thereby activate an administered photosensitizer at a therapeutically-effective wavelength to generate cytotoxic reactive species in the focal region. Another type of treatment unit may be a photoimmunotherapy subsystem configured to illuminate and thereby activate an antibody-photosensitizer conjugate bound to target cells with near-infrared illumination to induce cell-selective phototoxicity in the focal region.

Preferably, as will be described further below, one or more machine learning (ML) models (algorithms) are supported in the probe or in association therewith as components of the control unit first, second, third, and/or fourth portions. A given ML model 128 provides an inference (prediction) based on the model, which is pre-trained with a corpus of training data, typically using supervised learning, to distinguish normal versus abnormal tissue. Further details regarding the machine learning are described below.

In a representative use case, the first detection unit operates using SWE, the second detection unit operates using Raman, and the third detection unit operates via laser ablation, photodynamic therapy or photoimmunotherapy. According to an aspect of this disclosure, and as noted above, the probe includes the tracking unit that provides very fine-grained tracking data representing a displacement of a focal region of tissue, together with a predicted motion of the focal region over a given time horizon. Without intended to be limiting, the time horizon is on the order of milliseconds. There are several significant advantages provided by this arrangement. By way of background, a skilled person will appreciate that incorporating the ablation arm with the detection mechanisms within a single integrated probe creates many challenges, as the firing of the ablation arm necessarily occurs at a time and position distinct from the SWE and Raman inputs but still needs to target the same spot (referred to herein as the focal region of the tissue on interest). This is very challenging at least in part because the treatment beam in effect is attempting to hit a moving target. The same problem exists with respect to attempting to align the Raman beam with the EWG beam during the initial detection phrase. In both cases, the tissue of interest moves (in both 2D and 3D, as well as over time) for various reasons including physiologic (respiratory, cardiac, peristalsis), probe motion, hand or holder motion, and combinations of such factors. Accordingly, and to ensure that the Raman beam (during detection) and the treatment beam (during treatment) hits the desired target area, the tracking unit is configured to determine when residual motion of the focal region is at or below a pre-defined or configurable threshold value. Preferably, the Raman beam (for detection) and as necessary the treatment beam (for treatment) is activated. In accordance with a further aspect the pre-defined or configured threshold value may have associated therewith a confidence level, such that the beam (detection or treatment) is only activated when the motion of the tissue is at or below the threshold according to a given confidence level. To this end, and in a preferred embodiment, the tracking unit receives one or more input signals from which the motion of the tissue is ascertained. The tracking unit includes one or more sensors, such as an ultrasound displacement tracking sensor (e.g., on the same transducer that does SWE), an optical surface tracking sensor, an IMU (Inertial Measurement Unit) sensor, an electromagnetic sensor, and one or more sensors for detecting the physiologic references (ECG-mid-diastole, respiratory/ventilator signal (end-expiration), and the like). In a typical embodiment, the tracking unit is configured and operated in associated with the control unit software (or more generally the probe "controller" function) to identify the windows of minimal motion. This software is sometimes referred to herein as a motion engine. For example, the motion engine continuously estimates a displacement vector of the focal region and predicts short-horizon motion (20-150 ms); it then gates the Raman spectroscopy and treatment therapy, as the case may be, to align with the periods of minimal motion. In an alternative embodiment, the controller actively compensates one or both of these beams by beam-steering or micro-positioning (of the applicable unit(s)) so that residual motion at the focal region is less than or equal to the threshold.

Figure 2:
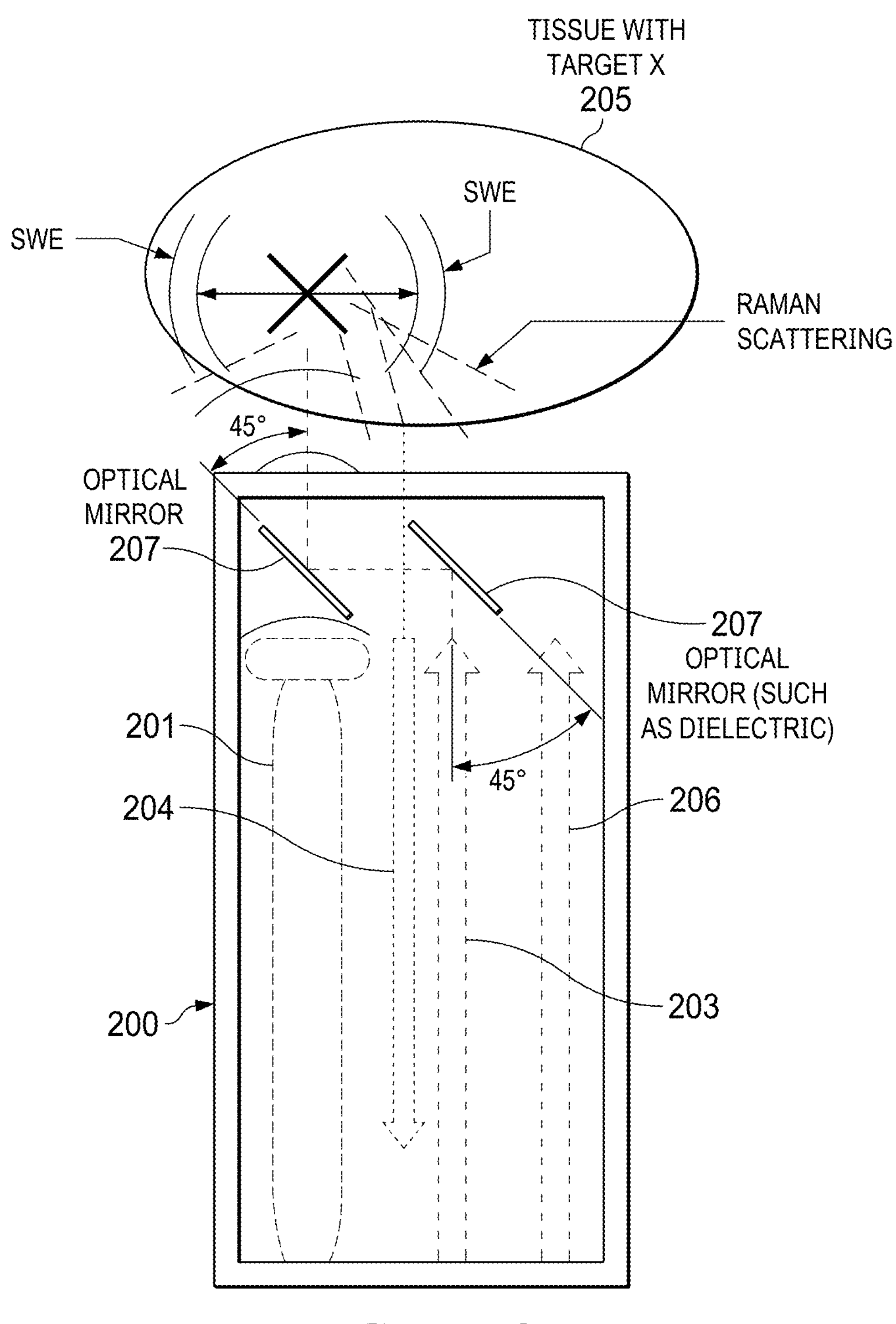
FIG. 2 depicts the SWE and Raman units of the multimodal interoperative probe in use during a measurement operation.

According to a further aspect of this disclosure, each of the two detection modalities and the treatment modality are distinct from one another. Because each modality must target the same focal region, the probe is configured to ensure that each beam output by a particular modality is output along substantially the same output axis. To this end, and as noted, the first detection unit (SWE), the second detection unit (Raman), and the third treatment unit output their respective first, second and third output beams along respective first, second and third axes that are co-aligned so as to selectively converge one or more of the first, second and third output beams on the focal region of tissue. This is depicted in FIG. 2. In this example, an output portion of the probe housing 200 is shown at bottom The focal tissue is depicted at 205. In this example, the SWE unit (see FIG. 1) outputs first beam 201, the Raman unit outputs the second beam 203 with signaling 204 returned, and (in this example) the PDT unit outputs the third beam 206. One or more acoustic and optical beam positioning/directing components, such as dielectric mirrors 207, are provided to direct one or more the beams onto the focal tissue target 205. In this example, the beams 201, 203 and 206 are depicted as slightly separated from one another, but a skilled person will appreciate that the beam(s) are output along axes that are substantially co-aligned. As necessary, the acoustic and optical beam positioning/directing elements further facilitate the co-alignment of the beams to ensure that the Raman beam appropriately aligns with the SWE beam, and further that the treatment beam targets the same target as do the detection beams.

Figure 3:
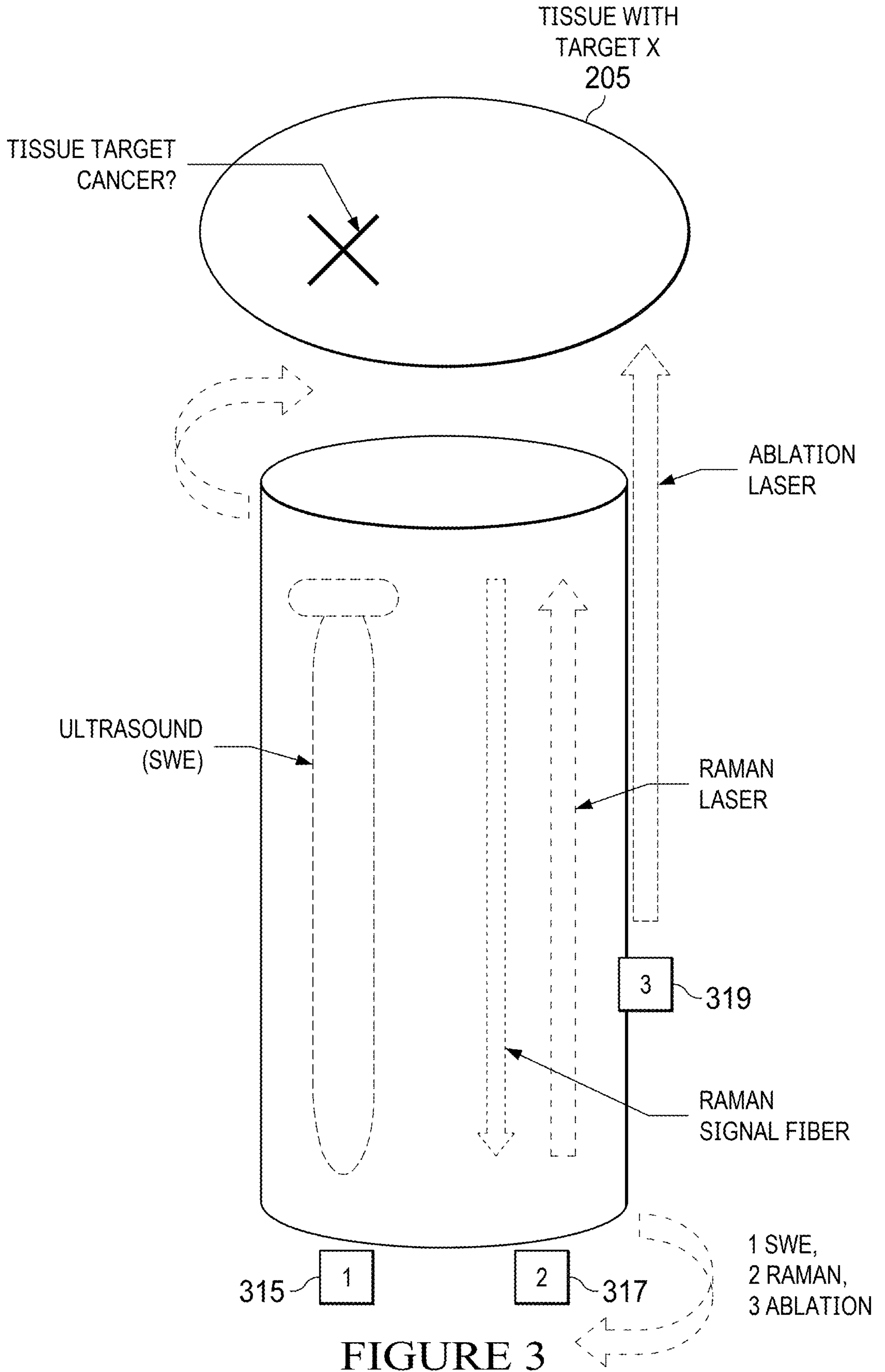
FIG. 3 depicts the PDT unit in operation to photo-ablate tissue based on the SWE or Raman findings.

FIG. 3 depicts another example of this axial beam co-alignment, together with a set of one or more activation buttons 315. As in FIG. 2, the co-alignment of the first, second and third axes are exaggerated for purposes of illustration. In use, the surgeon (or other user) activates the first button 315 to initiate the SWE operation. When the tracking unit then determines that the tissue of interest has a minimal motion, the second button 317 is activated to trigger the Raman unit. If diseased tissue is then indicated, the user activates the third button 319 to initiate the treatment beam. The number, type and operation of the buttons may vary. In actual use, and as described above, the acoustic and optical axes for the first and second detection units are necessarily co-registered to converge on a same focal region of tissue. As explained, and once the output beams are configured in this manner, the probe controller is operable to estimate/predict tissue motion and gate and/or actively track the focal region such that residual motion is less than or equal to a threshold, and to selectively arm therapy when the alignment/motion/confidence thresholds are met. Similar beam alignments are then carried out to re-scan the same focal region after ablation to confirm tissue margin clearance.

Summarizing the operation in one embodiment, the probe is then used as follows: (i) the shear wave elastography (SWE) transducer and sensors on the device (comprising the SWE unit) are activated to receive data regarding the macroscopic nature of the tissue of interest (stiffness or elasticity); (ii) the Raman laser and associated Raman detector (comprising the Raman spectroscopy unit) are activated to receive inelastic Raman spectroscopy data and molecular signature of the same tissue; (iii) the detected data is received and processed, and fused results of the machine learning algorithms (sometimes referred to herein as late fusion) are displayed; (iv) a fluorescent antibody conjugate is injected, the fluorescent tissue is visualized, and the laser (of the PDT unit) is activated to photo-ablate the tissue if concordant with Raman or SWE positivity; (v) the Raman and SWE acquisition are then repeated to confirm no residual disease.

Figure 4:
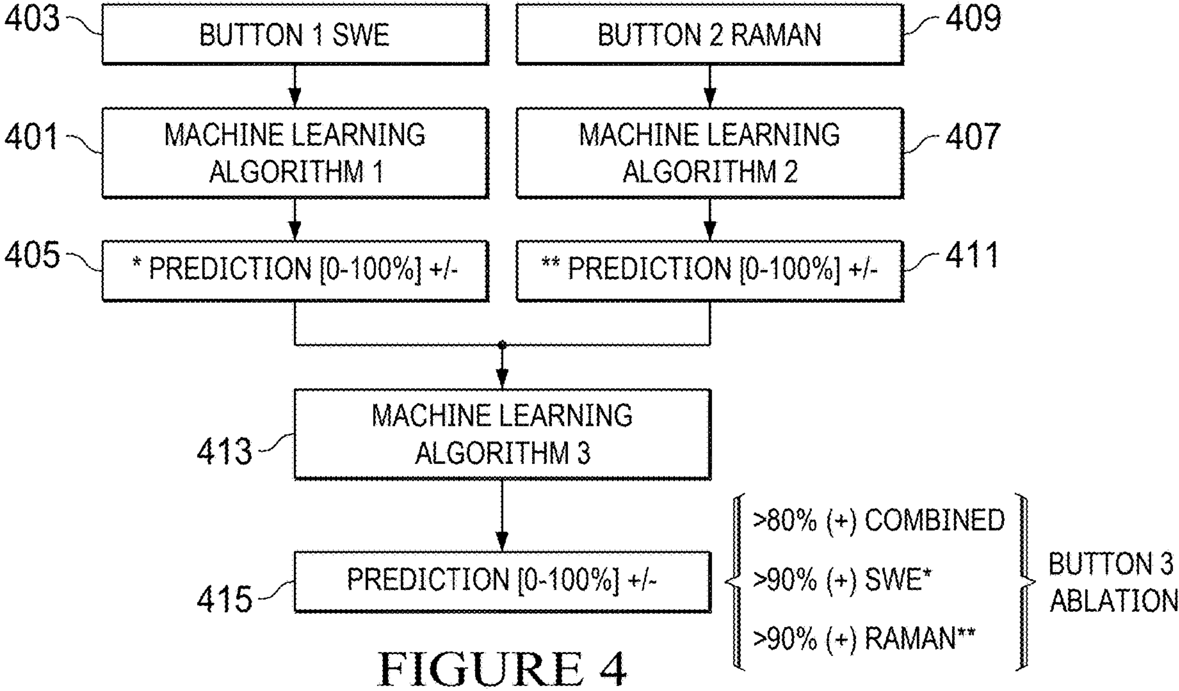
FIG. 4 depicts an operation of exemplary Machine Learning (ML) inferencing portions of the probe unit.

The following describes the machine learning and the notion of late fusion as referenced above. FIG. 4 depicts the process. When applying the probe to the surface of the unknown tissue, and as noted above in a representative operation, a fiberoptic cable transmits the scattered Raman data to the Raman unit detectors and the associated machine learning model (for the Raman data), previously trained and validated on normal and abnormal tissue. In a similar manner, the elastography modulus data collected by the SWE unit is processed and provided to an associated machine learning model (for the SWE data). Preferably, the data from the two modalities (Raman and SWE) in real-time would be independently analyzed, e.g., via machine learning, and subsequently combined to produce a probability reading on the device's gauge. In a variant, a third set of data, namely, the data obtained from Raman and shear wave elastography readings taken from the known excised cancerous tissue, is added to the machine learning (in effect as additional training data for the ML algorithms) in real-time to increase the precision of the device. In particular, adding real-time data in this manner provides a way to further train (augment or supplement) the device model(s) so that they are more specific to the case at hand, thereby providing a more precise prediction to be obtained. This data typically is patient-specific, e.g., based on a differential diagnosis by a pathologist that tissue is or is not diseased. This type of patient-specific data may be used to augment the determination of whether particular tissue should be treated; the data may also be used to augment a confidence level associated with the output(s) generated by the machine learning model (s). In FIG. 4, there are separate machine learning models, e.g., for each modality, although this is not a requirement, as a single ML model may be trained with sufficient training data and then used for inferencing on the detected tissue. In particular, a machine learning algorithm (model) 401 is associated with the SWE unit 403, and model 401 generates prediction 405; likewise, a machine learning algorithm (model) 407 is associated with the Raman unit 409 and generates prediction 411. A machine learning algorithm (model) 413 receives predictions 405 and 411 and generates the final prediction 415 (e.g., whether the tissue is normal or diseased). The models 401 and 407 typically have been pre-trained on corpora of training data specific to each respective modality (SWE, Raman).

In the example handheld probe embodiment, and as previously noted, the probe has a housing having a handle, and the handle supports one or more activation buttons for the various functions. The positioning of the activation buttons may vary. The shear wave elastography module with its ultrasound transducer is also located within the housing. A second button activates the ultrasound transducer, thereby generating data from which a calculated shear modulus is computed by the controller unit. In use, the shear waves travel perpendicular to the ultrasound beam, thereby displacing the soft tissue. The measurement of tissue displacement helps calculate the shear wave velocity, which correlates with the shear modulus. The shear wave modulus, in turn, correlates with the tissue elasticity. The shear wave speed is measured in meters/second (m/sec). The modulus is measured in kilopascals (Kpas). For the Raman operation, which typically occurs after the SWE and upon a determination of minimal tissue movement, a button connected to the controller unit activates the laser. Both the laser and the returning, scattered Raman signal are transmitted via fiber optics in the Raman probe, with the signal cable preferably running parallel to the laser fiber. As noted above, both the laser and signal cables preferably run together within the Raman probe.

The input data from the shear modulus is applied to a first machine learning model (e.g., an SVM), and the input data from the Raman spectra is applied to second machine learning model (e.g., a GBT). As depicted in FIG. 4, the outputs from both algorithms 401 and 407 merge to produce a late fusion of data to produce a prediction. As noted above, the predictions generated by the individual models (and the resulting merged prediction 415) may be further augmented by real time input data from the excised tissue.

The diagnostic result is displayed (e.g., on the display 124 depicted in FIG. 1) with a numerical quantitative reading (for example, 80% cancer probability, with a given confidence level), on a colorimetric display. The diagnostic result may also be generated audibly or by a tactile output on the device handle.

A third button on the device's handle activates the laser for the treatment, e.g., photodynamic therapy (PDT), based on the concordance of the Raman, SWE, and fluorescent tag analyses (the outputs of the machine learning). As is known, a fluorescent particle conjugated with an antibody specific for a tumor specific antigen tags the cancerous tissue of interest after a standard delay of time. A time delay between injection and assessment of fluorescent tissue is necessary to allow washout of circulating fluorescence. In this way, the visualized fluorescent tissue is more likely to represent the specific cancerous tissue. Reliance on only the fluorescent tag to identify the cancerous tissue, however, presents a too high possibility of a false positive result. Prior to initiation of laser ablation of the fluorescent tissue, the results from the Raman and SWE preferably are assessed for concordance.

Figure 5A:
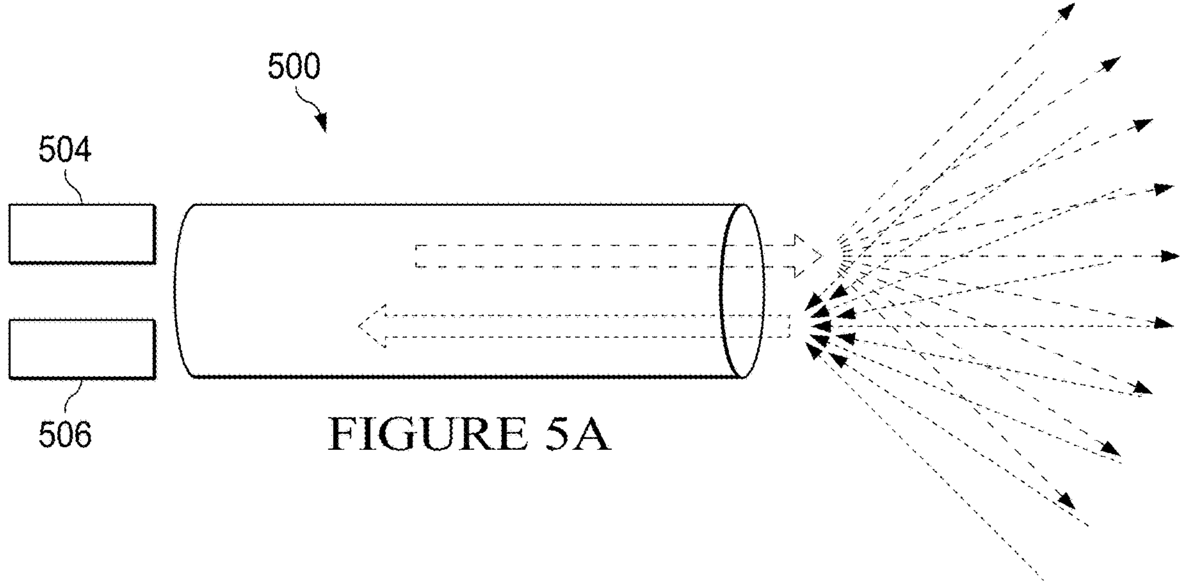
FIGS. 5A-5C depicts a variant embodiment wherein the multimodal interoperative probe is configured within a handheld wand that further comprises a set of Raman probes for imaging a large anatomical area of a patient.
Figure 5B:
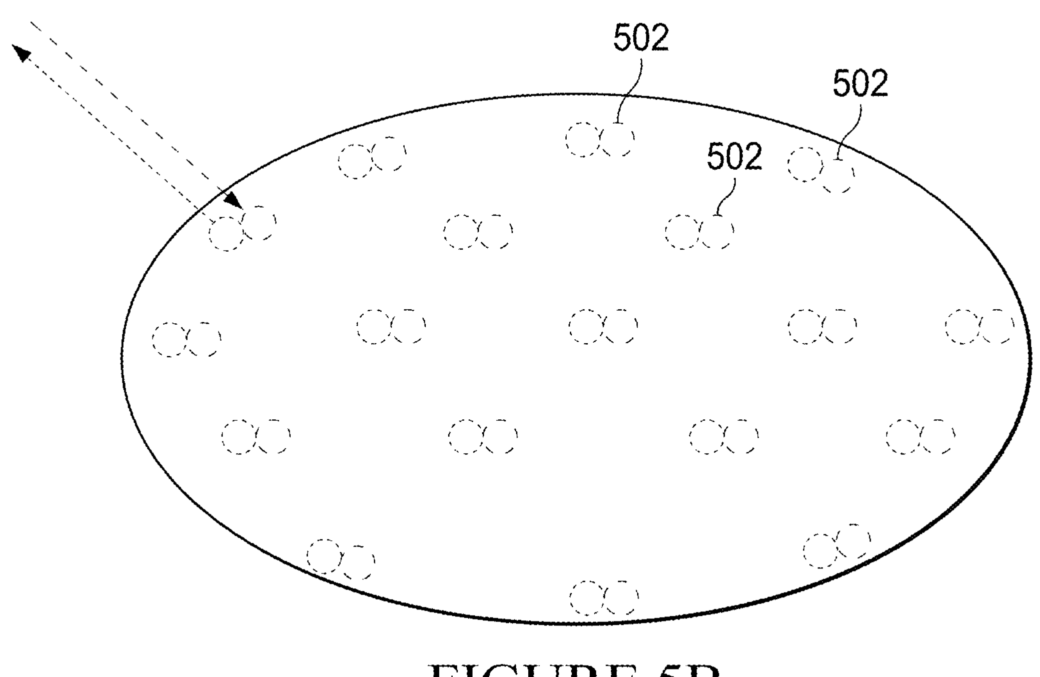
Figure 5C:
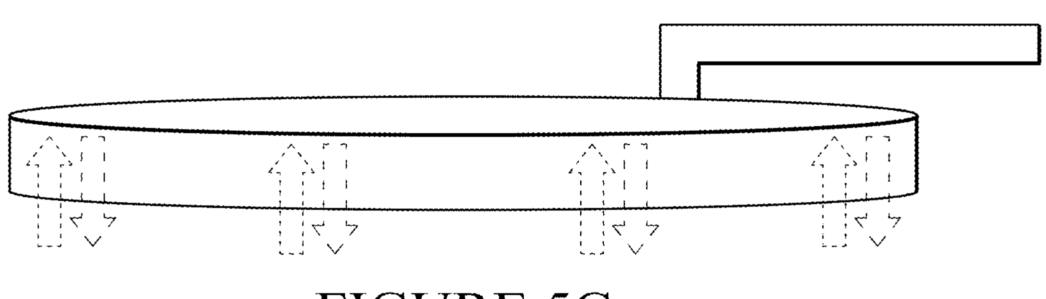

FIGS. 5A-5C depicts an alternate embodiment in the form of a spherical or round wand 500, embedded in which are multiple Raman probes 502 in the form of a laser 504 and adjoining signal detector (fiber optic) 506. A top view of a representative wand configuration is depicted in FIG. 5B. The multiple lasers can be generated by a laser beam splitter from a single laser source. This wand provides an overview of a large anatomical area, such as the peritoneal cavity. This variant may be used in the operating room as a final clearance or sweep before closure, or at the start of a procedure to provide the surgeon an overview of the anatomical area of interest.

In summary, in this embodiment the intraoperative probe houses a Raman spectroscopy-based probe, an SWE transducer, and a laser for PDT. When used by a surgeon, the surgeon's hand controls each of the individual modalities, preferably with individuals buttons on the handle, although one or more control functions may also be programmable. The device is applied to the surface of the tissue with minimal pressure. As depicted in FIGS. 2-3, the Raman probe typically comprises a 780 nm laser. The PDT laser ablation unit may use the same 780 nm laser, thereby obviating a second laser cable, or a separate 630 nm laser. To focus the Raman probe laser on the same focal point as the ultrasound (SWE), an optical mirror is used for the laser. Alternatively, the Raman probe is configured to be rotated to the same position as the ultrasound beam. Rotation may be effected manually or electrically-controlled. In the latter case, mechanical positioning elements (controlled by the controller unit) are also included within the housing.

As mentioned, the training of the machine learning model (s) here typically occurs off-line, i.e., prior to the use of any such models for the real-time inferencing during use of the intraoperative probe during an actual surgical procedure. Typically, supervised learning techniques are used for training.

The nature and type of Machine Learning (ML) algorithms that are used to process the patient-captured data (from other patients) into one or more data models may vary. The ML algorithms iteratively learn from the patient-captured data, thus allowing the system to find hidden insights without being explicitly programmed where to look. ML tasks are typically classified into various categories depending on the nature of the learning signal or feedback available to a learning system, namely supervised learning, unsupervised learning, and reinforcement learning. In supervised learning, the algorithm trains on labeled historic data and learns general rules that map input to output/target. The discovery of relationships between the input variables and the label/target variable in supervised learning is done with a training set, and the system learns from the training data. In this approach, a test set is used to evaluate whether the discovered relationships hold and the strength and utility of the predictive relationship is assessed by feeding the model with the input variables of the test data and comparing the label predicted by the model with the actual label of the data. The most widely used supervised learning algorithms are Support Vector Machines, Linear Regression, Logistic Regression, Naive Bayes, and Neural Networks.

In unsupervised machine learning, the algorithm trains on unlabeled data. The goal of these algorithms is to explore the data and find some structure within. The most widely used unsupervised learning algorithms are Cluster Analysis and Market Basket Analysis. In reinforcement learning, the algorithm learns through a feedback system. The algorithm takes actions and receives feedback about the appropriateness of its actions and based on the feedback, modifies the strategy and takes further actions that would maximize the expected reward over a given amount of time.

The following provides additional details regarding supervised machine learning, which is the preferred technique used in the learning approach herein. As noted above, supervised learning is the machine learning task of inferring a function from labeled training data. The training data consist of a set of training examples. In supervised learning, typically each example is a pair consisting of an input object (typically a vector), and a desired output value (also called the supervisory signal). A supervised learning algorithm analyzes the training data and produces an inferred function, which can be used for mapping new examples. An optimal scenario allows for the algorithm to correctly determine the class labels for unseen instances. This requires the learning algorithm to generalize reasonably from the training data to unseen situations.

For supervised learning, the following steps are used. An initial determination is what kind of data is to be used as a training set. Here, the training data preferably are Raman spectra and SWE-related data captured from other patients using the device configuration described above. The training set is then gathered. In particular, during the training phase, and for each laser source and receiver combination, the absorption spectrum or other detected data is measured, quantized, and digitized. An input feature vector for each patient (in the training data set) preferably comprises of such measurements from each source and receiver pair, along with corresponding information about the positioning and orientation of the pair, any metallic coatings and laser wavelength etc.

The use of separate machine learning models as described above provides advantages. Because in the described embodiment the two models are trained on distinctly different types of data (here a first set has data related to molecular analysis (Raman), and a second set has data related to stiffness or strain (SWE)), one has a choice of combining the many separate variables into one model, or to create training and testing data from each model independently of the other and later combine the results and merging the conclusions from each model into a final model. Using the approach, the modeling provides for the ability of the trained system to arrive at a probability (that the tissue of interest is cancer, or not) via two (2) different pathways. While one of the pathways may provide better predictive capability than the other, an improved prediction is enabled by the combined approach as contemplated. In a variant embodiment, just a single prediction (e.g., from a single model) may be used.

While as described herein Raman spectroscopy is a preferred approach for use in the probe and in the method, other techniques that could be substituted for, or used in combination with, Raman spectroscopy include, without limitation: single-photon confocal fluorescence microscopy; multiphoton excitation microscopy (two-photon and three-photon); second-harmonic and third-harmonic generation (SHG/THG) microscopy; fluorescence lifetime imaging microscopy (FLIM); stimulated Raman scattering (SRS) microscopy; coherent anti-Stokes Raman scattering (CARS) microscopy; tip-enhanced Raman spectroscopy (TERS); surface-enhanced Raman spectroscopy (SERS); spatially offset Raman spectroscopy (SORS) and shifted-excitation Raman difference spectroscopy (SERDS); hyperspectral and multispectral imaging; diffuse reflectance and elastic scattering spectroscopy; optical coherence tomography (OCT), including polarization-sensitive OCT and OCT angiography; quantitative phase and interferometric/holographic microscopy (e.g., digital holographic microscopy); Brillouin light scattering/microscopy for biomechanical contrast; photoacoustic imaging/spectroscopy (PAI/PAM); laser-induced fluorescence (LIF) and laser-induced breakdown spectroscopy (LIBS); near-infrared spectroscopy (NIRS), including short-wave infrared/NIR-II fluorescence imaging; spatial frequency domain imaging (SFDI) and diffuse optical tomography (DOT); surface plasmon resonance (SPR) and localized SPR (LSPR); scanning near-field optical microscopy (SNOM/NSOM); super-resolution fluorescence methods (STED, SIM, PALM/STORM); atomic force microscopy (AFM); electron microscopy (TEM/SEM) for ex vivo analysis; mass spectrometry and ambient ionization variants (e.g., DESI, DART, REIMS); ultraviolet-visible (UV-Vis) spectrophotometry; Fourier-transform infrared (FTIR) spectroscopy, including attenuated total reflectance (ATR-FTIR); X-ray fluorescence (XRF); and combinations thereof.

Further, while as described herein SWE is a preferred approach for use in the probe and in the method, other techniques that could be used in addition to, or implemented as variants of SWE include, without limitation: quasi-static (compression/strain) elastography (manual or physiologic motion); transient elastography, including vibration-controlled transient elastography (VCTE); acoustic radiation force-based methods such as ARFI imaging, shear-wave elasticity imaging (SWEI), point SWE (pSWE), and 2D/3D-SWE (e.g., plane-wave ultrafast and supersonic implementations); shear-wave dispersion ultrasound vibrometry (SDUV) and related viscoelastic parameter mapping (e.g., storage/loss moduli, viscosity); reverberant and crawling-wave elastography; passive elastography using intrinsic or ambient vibrations (cardiac/respiratory); harmonic motion imaging (HMI); vibro-acoustography and Doppler-based sonoelastography; acoustoelasticity imaging (stress-dependent speed/attenuation); poroelastography; microbubble-mediated ARFI and acoustic micro-tapping; acoustic microscopy; acoustic interferometry; optical elastography modalities including optical coherence elastography (OCE) (phase-resolved, dynamic, magnetomotive), laser speckle rheology, optical micro-elastography, and Brillouin microscopy; photoacoustic elastography; magnetic resonance elastography (MRE); as well as instrumented tactile/impedance imaging (force/pressure-sensor-based palpation tomography integrated into the probe), endoscopic/laparoscopic elastography, and intravascular ultrasound elastography; and combinations thereof.

Still further, while as described herein laser-PDT elimination of the detected cancer is a preferred embodiment, other techniques for cancer elimination could be used. These include, but are not limited to, laser ablation, plasmonic nanoparticles, and quantum dots with thermal tissue monitoring. Additional methods of cancer destruction housed in the probe can include, but are not limited to, high-intensity focused ultrasound, and femtosecond or picosecond laser pulses. Techniques to minimize thermal collateral damage of adjacent tissue include precise targeting coupled with ablation cooling and other thermal mitigating technologies. Thus, for example, the ablation module of the multimodal probe includes an attosecond pulsed laser source configured to deliver energy via a fiber-optic cable, hollow-core waveguide, or photonic integrated platform. The laser source of this type generates pulses with durations in the range of 50 to 500 picoseconds, suitable for non-thermal, ultrafast ablation with minimal collateral tissue damage. The femtosecond or picosecond pulses may be produced through high-harmonic generation (HHG) in a remote source and transmitted to the probe tip or may be generated locally via waveguide-based nonlinear optics embedded within or adjacent to the probe housing.

Regardless of the targeting system and technology used, the pulse delivery system is aligned co-axially with the diagnostic modalities (e.g., Raman spectroscopy and shear wave elastography), enabling precise, spatially co-registered ablation of tissue classified as malignant. The ultrafast pulse width is preferred, as it enables ablation mechanisms driven by electron-level interaction, reducing the reliance on thermal diffusion and thus preserving adjacent healthy structures.

Generalizing, during the destroy operation on the identified diseased tissue parameters such as power and dwell time are adjusted. Additionally, PDT-based technologies may be augmented using agents like protoporphyrin IX (PpIX) or antibody-conjugated fluorescent markers.

As a further feature, and as described above, a machine learning model used within or in association with the probe is further trained (or the existing training is further reinforced) on data obtained from using the above-described detection mechanisms of the probe on the patient himself/herself. In this way, the actual surgical operation can begin with system that has been custom-trained for the patient.

Figure 6:
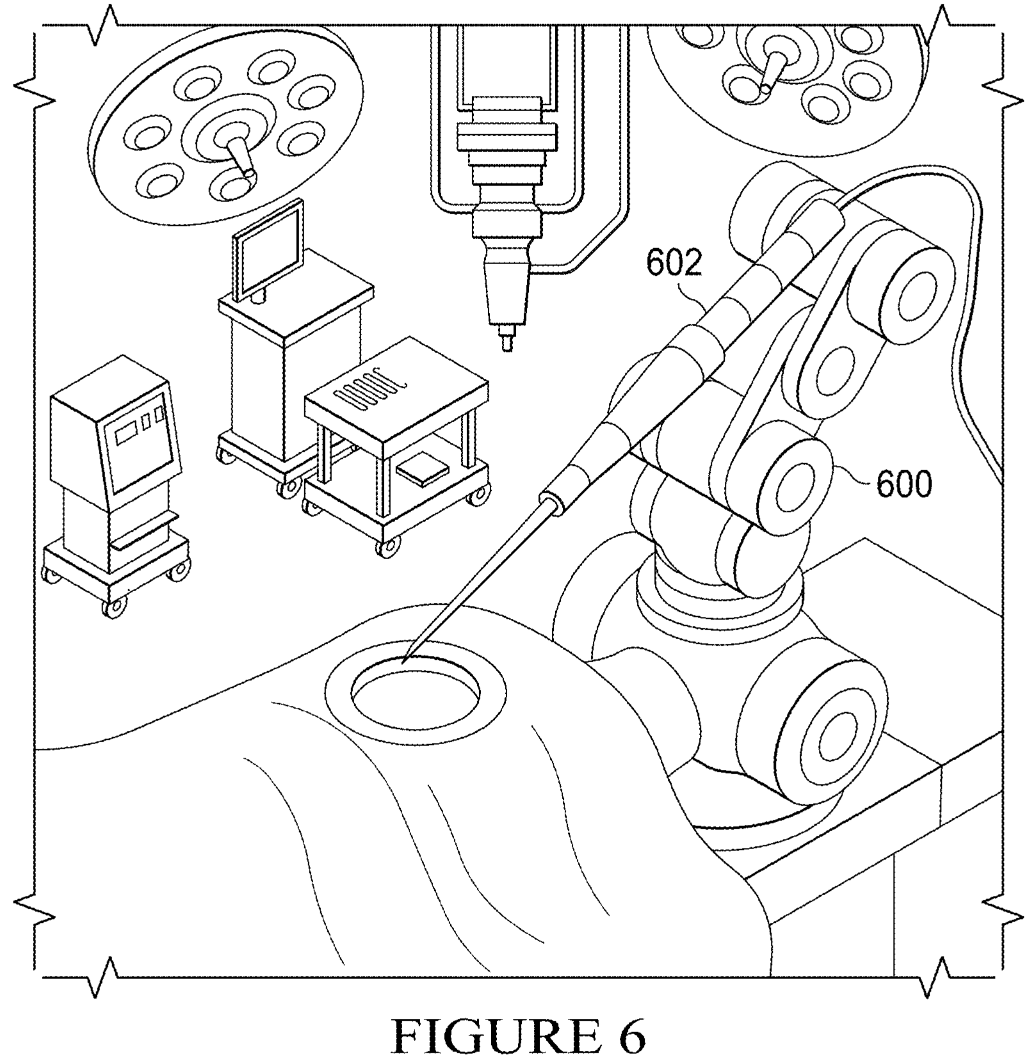
FIG. 6 depicts an alternative embodiment wherein the multimodal interoperative probe is mounted on a robotic system or assembly for autonomous or semi-autonomous operation.

The multimodal interoperative surgical probe describing herein may be integrated with a robotic surgical platform. This embodiment is depicted in FIG. 6, wherein the probe 602 is affixed to a robotic arm 600 such as a Da Vinci surgical robot, a KUKA industrial robot, or a custom-designed six-degree-of-freedom (6DOF) arm. In this embodiment, navigation coordinates obtained from the probe's spatial tracking module and fused imaging data are transmitted to a robotic controller. This enables the system to perform semi-automated targeting of the tissue of interest or to execute a pre-defined ablation path with sub-millimeter precision. The robotic integration enhances stability, minimizes operator variability, and allows for precise delivery of diagnostic and therapeutic modalities, particularly in anatomically constrained or motion-affected surgical fields.

Figure 7:
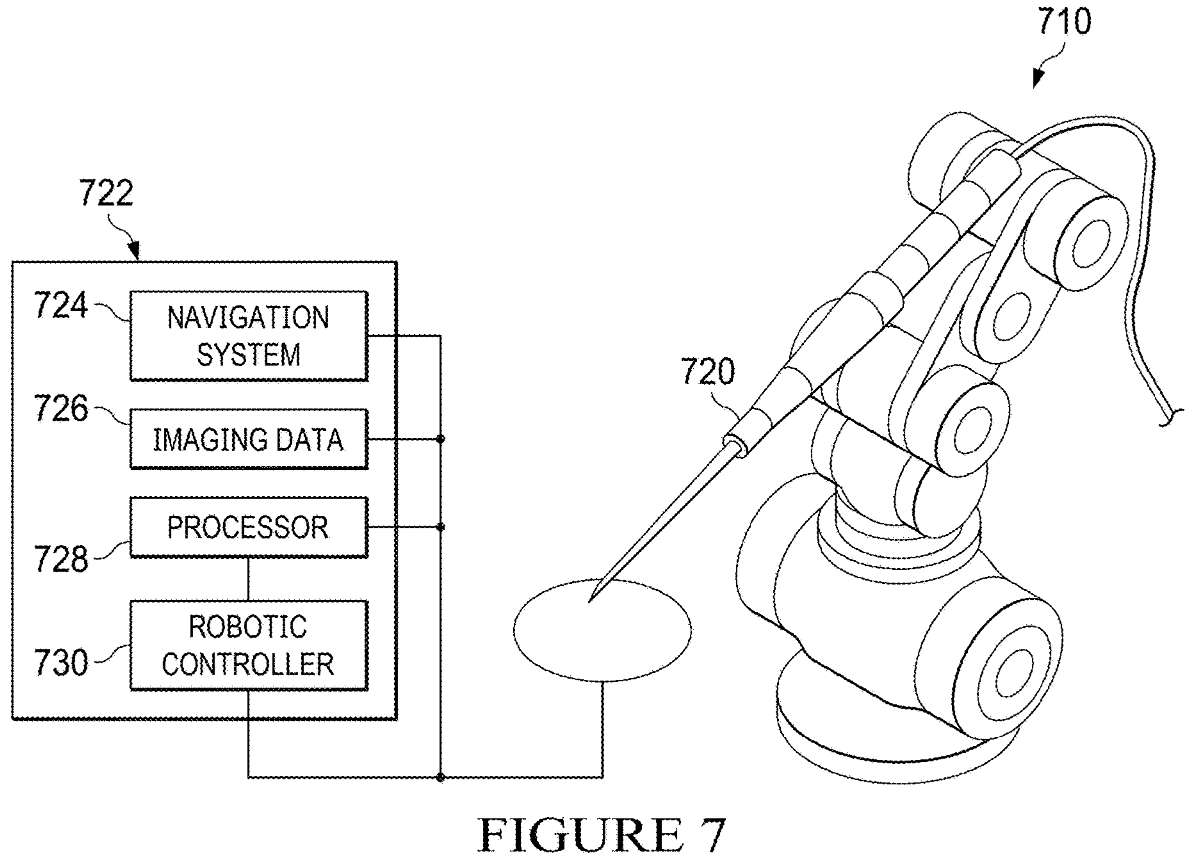
FIG. 7 depicts a system integrating the multimodal surgical probe with a robotic arm and its associated control system.

FIG. 7 depicts a more detailed schematic diagram illustrating an integration of a multimodal intraoperative surgical probe with a robotic surgical platform. In this example, the robotic surgical platform includes a robotic arm assembly 710 comprising a multi-jointed, motorized manipulator capable of six degrees of freedom (6DOF) movement. As depicted, the multimodal surgical probe 720 is mounted at a distal end of the robotic arm. In this embodiment, the probe

720 integrates Raman spectroscopy optics, a shear wave ultrasound transducer, and a picosecond pulsed laser ablation fiber into a single, co-axially aligned unit. The robotic system receives real-time spatial positioning data and diagnostic input via a navigation and control system 722, which comprises a combination of 3D optical tracking modules, electromagnetic field sensors, and AI-powered data fusion algorithms. In this embodiment, the system 722 comprises navigation system 724, imaging data processing system 726, one or more processors 728, and a robotic controller 730. This control system interprets imaging and tracking data to calculate optimal probe positioning and ablation trajectories. The robotic controller then translates these commands into fine-grained motion adjustments of the robotic arm 710, enabling sub-millimeter accuracy for diagnostic sampling and therapeutic laser delivery. By integrating robotic precision, multimodal diagnostics, and closed-loop control, the system enables semi-automated or fully guided targeting of suspicious tissue zones during surgery. The result is enhanced accuracy, minimized operator error, and improved intraoperative cancer clearance.

Figure 8:
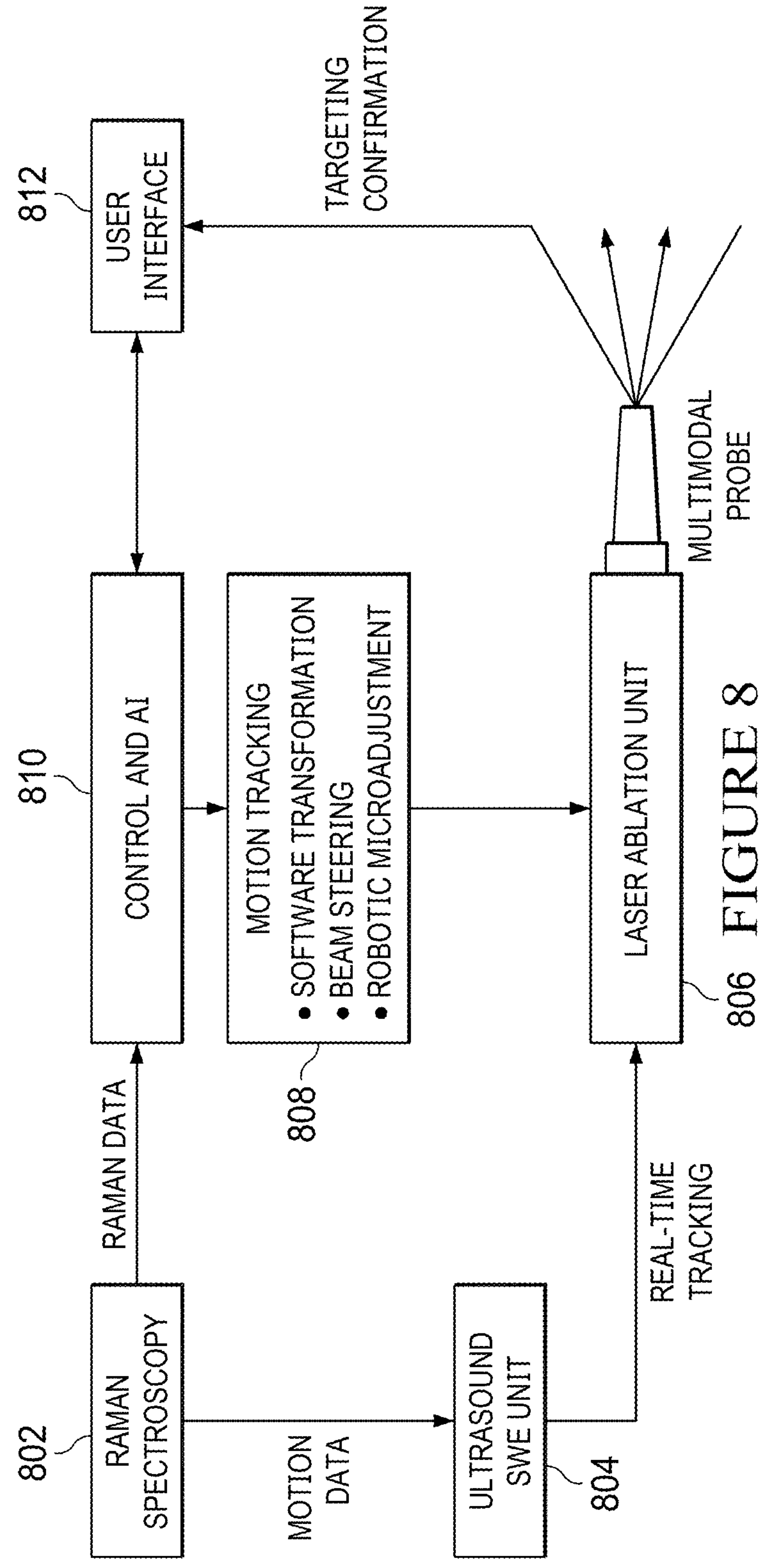
FIG. 8 depicts a system block diagram of one preferred embodiment that provides real-time multimodal targeting with motion compensation and other safety features.
Figure 9:
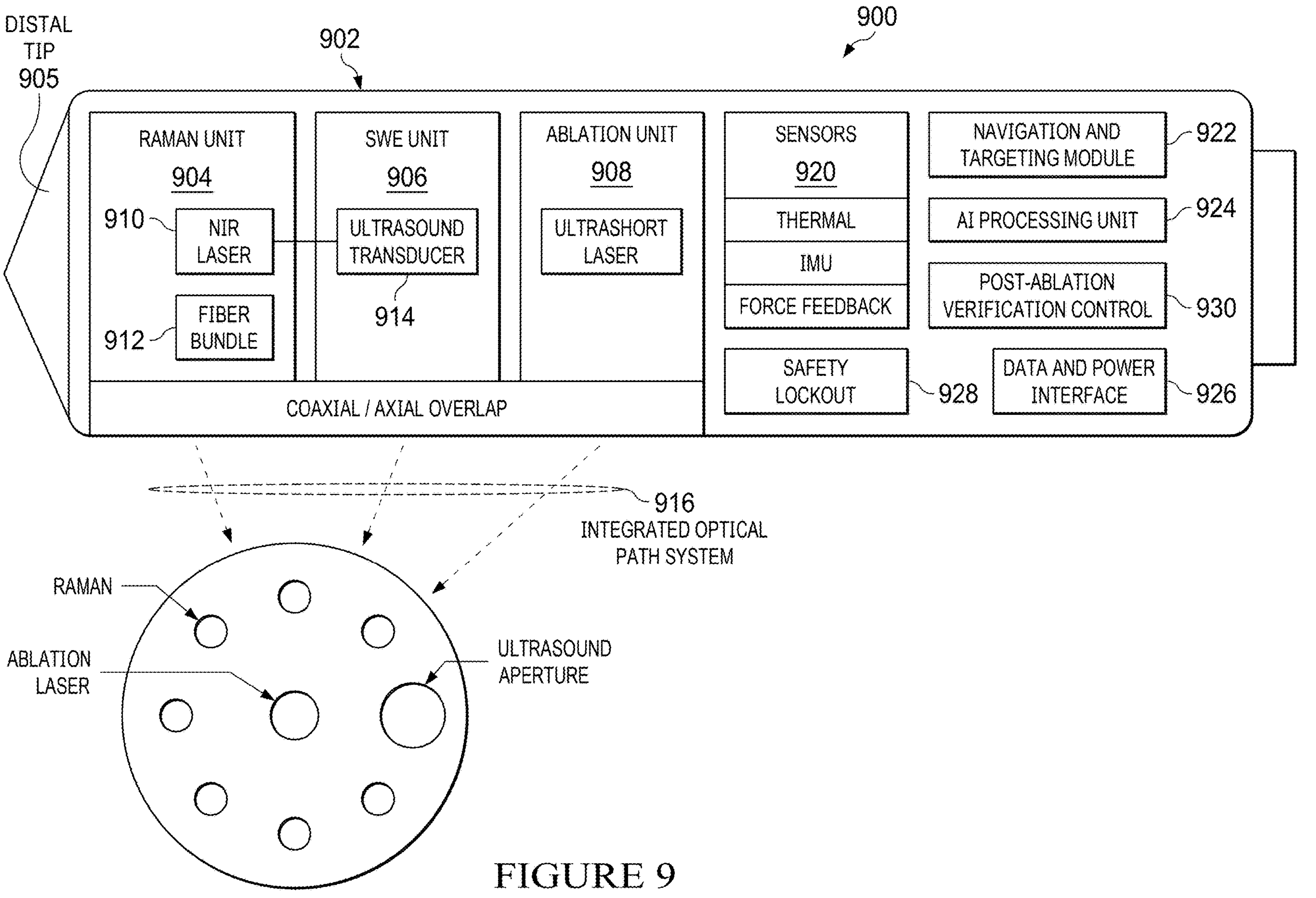
FIG. 9 depicts an alternative probe configuration that exhibits Raman fast scanning.

FIG. 8 illustrates a block-level system diagram of a multimodal intraoperative surgical probe integrating real-time motion compensation for precise co-alignment of diagnostic and therapeutic modalities. This system may be implemented in association with the handheld probe, or the robotic system-supported probe. As previously explained, the probe comprises three core subsystems to provide the multimodal operation: the Raman spectroscopy unit 802, the shear wave elastography (SWE) ultrasound unit 804, and the attosecond pulsed laser ablation module 806. The SWE module 804 acts as a reference anchor modality, continuously acquiring tissue displacement data at high frame rates. This data is used to detect subtle tissue motion, such as that caused by respiration or cardiac pulsations. The Raman spectroscopy unit 802 preferably is software-synchronized to operate only during periods of minimal tissue motion, optionally triggered by physiological gating (e.g., ECG or respiratory phase). In this embodiment, the femtosecond or picosecond laser ablation module 806 is controlled by the motion tracking unit, e.g., a motion compensation engine 808. This engine incorporates software-based spatial coordinate transformation, real-time beam steering (e.g., via MEMS mirrors), and/or mechanical repositioning of the probe tip (e.g., robotic arm or gimbal-based system) to maintain alignment with the moving target tissue. A centralized control and AI fusion module 810 independently analyzes input data from both Raman and SWE modalities. Upon classifying tissue as malignant, the system confirms alignment across all modalities. In response, a trigger signal sent to the laser ablation unit 806, subject to safety thresholds and lockouts. The user interface (UI) 812 displays, preferably in real-time, tissue classification probabilities, alignment status, and active targeting zones. To this end, optional overlays or augmented reality (AR) interfaces may be incorporated to allow the surgeon to visualize the active target area dynamically. This closed-loop system ensures that diagnostic readings and therapeutic actions are co-localized, synchronized, and verified in real-time, even when target tissue is undergoing subtle physiological motion. The result is a high-precision, safety-enhanced intraoperative cancer treatment workflow. Generalizing, and once a determination that disease tissue has been identified, the probe system integrates motion sensors and real-time image analysis to adaptively adjust ablation parameters (e.g., energy, pulse width, focus) based on tissue movement, position drift, or unanticipated anatomical features.

With reference to the system diagram in FIG. 8, the preferred workflow incorporates Raman spectroscopy, shear wave ultrasound, and femtosecond or picosecond pulsed laser ablation modules. The SWE unit provides continuous tracking of tissue motion, serving as the anchor modality. The data generated by the SWE unit includes spatial tracking data and, in particular, spatial coordinates of an SWE-tracked target (typically an area of tissue). The Raman spectroscopy unit is coaxially aligned (sometimes referred to herein as co-registered) to the spatial coordinates of the SWE-tracked target using a common coordinate frame. The Raman spectroscopy and laser ablation modules are triggered based on gated timing and spatial alignment. The motion compensation engine processes ultrasound-based tissue shifts and updates targeting using software correction, MEMS-based beam steering, or (in the robotic-based embodiment) robotic adjustments. For example, motion compensation may involve one or more of: digital coordinate transformation, beam steering using a galvanometer or MEMS mirror, robotic micro-adjustment of the probe tip, and autofocus based on real-time depth sending. The controller and AI engine fuse Raman and SWE data, apply safety lockouts, and manage phase-based firing (e.g., end-diastole). Raman data acquisition and/or laser ablation are triggered during physiologically-stable moments, e.g., as determined by ECG, respiratory gating or otherwise, and co-localization of the Raman, SWE and laser ablation targets are verified prior to activation of the laser ablation module. During this operation, and depending on implementation, the skill of the operator or other factors, the user interface UI displays real-time classification, a guidance overlay, and one or more verification prompts. The system functions in a closed-loop architecture to ensure precise alignment and ablation (including microscale intraoperative targeting) despite physiologic motion (including due to breathing, heartbeat, peristalsis, etc.).

The following provides further implementation details of a multimodal intraoperative probe 900. The probe 900 comprises a housing 902, typically a cylindrical-shaped shaft containing and supporting internal diagnostic and therapeutic modules, including the Raman spectroscopy unit 904, the SWE unit 906, and the ablation laser unit 908. The Raman spectroscopy unit 904 typically is located near a distal tip 905 of the probe and incorporates a Near-Infrared (NIR) laser (e.g., 830 nm) 910 and fiber-optic bundle 912 to excite and collect Raman signals from the tissue. The SWE unit 906 is an ultrasound transducer 914 that is typically mounted adjacent to the Raman optics with coaxial alignment (axial overlap) to measure tissue elasticity. The ablation laser unit 908 delivers ultrashort laser pulses (<500 fs) for photothermal or photodynamic tissue destruction. Laser wavelengths for ablation laser typically range from 1064-1470 nm. The probe in this embodiment includes an integrated optical path system 916 (mirrors, prisms, beam splitters and beam combiners) that aligns Raman, SWE and ablation beams to a common focal point within the area of the tissue of interest. The probe here also includes an embedded cooling system 918, e.g., microchannel coolant pathways or thermoelectric modules to reduce thermal spread during operations of the laser(s). Further, the probe includes a suite of sensors 920, such as thermal sensors, inertial motion units (IMU), and force feedback sensors for real-time interaction monitoring. A navigation and targeting module 922 provides for 3D optical tracking, or visual SLAM (Simultaneous Localization and Mapping). SLAM is a technique that enables a robot or device to build a map of an environment while simultaneously determining its own location within that map using visual data from a camera or multiple cameras. It allows the device to navigate and understand its surroundings by processing visual information. The module 922 may also include electromagnetic sensors to localize the probe in real-time. The navigation and targeting module may be integrated with surgical navigation overlays or AR systems. An AI processing unit 924, which may be on-board in the probe housing or located externally, runs the ML models (e.g., a Gradient Boosted Tree (GBT), a Convolutional Neural Network (CNN), or the like) for separate analysis of Raman and SWE data, followed by ensemble-based fusion of the results for malignancy determination and classification. A data and power interface 926 provides a fiber-optic and power cable link to an external interface or controller. A safety lockout mechanism 928 is configured to prevent laser ablation unless malignancy is confirmed and one or more safety criteria (e.g., tissue distance, navigation confirmation) are first satisfied. The probe may also include a post-ablation verification interface or controller 930 that re-activates the Raman and SWE modules for scanning ablated tissue margins, and displays confirmation data on an associated UI or monitor, or a Heads-up Display (HUD).

According to a further aspect, the probe provides for real-time Raman spectroscopy and ultrasound SWE integrated into the probe for fast (5×5 cm) tissue scanning, e.g., during abdominal cancer resection surgery. To this end, and using wide-field Raman spectroscopy, the acquisition time is potentially as lows as 0.5-1.0 second for a 1 mm area. To achieve the fast tissue scanning, multi-line Raman illumination is combined with a slit-array spectrometer, allowing for parallel detection of multiple spectra with a single camera exposure; this enables under one second tissue characterization. A probe configuration that provides this fast Raman acquisition comprises an excitation module in the form of a multiline laser system to provide single multimode fiber or split-to-fiber bundle beam delivery. For example, a system of this type comprises a set of lasers (e.g., 532 nm, 660 nm, 785 nm and 1065 nm diode lasers), at a power rating of 20-80 mW per line, with a combiner in the form of dichroic mirrors or a wavelength division multiplexer (WDM). The multiline excitation improves tissue contrast (i.e., normal tissue versus a tumor) by targeting different Raman bands. In a specific implementation, the head of the probe comprises a fiber bundle (e.g., 61-121 fibers), each 200-300 μm core, with each fiber having a circular or square footprint approximately 5 mm diameter (approximately 1 $cm^2$). The bundle includes excitation fibers (a central delivery or side illumination ring (3-6 fibers), and a set of collection fibers, with preferably each fiber linked to a spectrometer input channel. The fibers typically comprise biocompatible (fused silica), with autoclaved casing. The probe head allows scanning a wide field without moving the probe tip extensively. The probe in this embodiment also includes a detection system that provides parallel spectroscopy. The detection system comprises a multichannel spectrometer with 8-16 ports, gratings optimized for each laser, high quantum efficiency, low noise detectors such as EMCCD or sCMOS per channel, and a spectral range (biological window) of 400-1800 $cm^{-1}$. Acquisition time of the detectors is on the order of approximately 10-50 ms/spectrum per fiber. The probe control and classification software, which may be on-board or remotely-accessible, provides for laser control (e.g., TTL/synchronized switching between lasers), data acquisition (Raman spectra from all channels), signal processing (baseline correction, other noise removal), machine learning-based or other tissue classification (SVM, GBT, CNN, other deep learning, PCA, etc.), display (e.g., color-coded tumor margin overlay on a probe view or tissue map) and system integration (e.g., operating room-compatible touchscreen, HMD, or the like). The probe form factor varies depending on implementation (handheld, laparoscopic-compatible, surgical clamp-supported, robot assembly-supported, etc.) As additional options, the probe includes an autofocus or distance sensor to optimize focus when the tissue of interest has surface curvature, a white light co-illumination module to enhance visual and Raman operations, a fluorescence rejection filter to provide better Raman signaling, and integrated suction/irrigation tools to ensure that tissue remains clear during surgery. For sterility, a detachable sterile sheath or autoclavable support components may be included. In operation the multiline laser system drives the fiber bundle to excite tissue at several points and bands, and to collect the Raman signaling, with those signals sent to the parallel detectors in the spectrometer, processed and classified in real-time, and providing an output visual margin feedback to the surgeon. This enables real-time (ultrafast) intraoperative identification of cancerous tissue margins and associated tissue classification, which is particular useful in abdominal cancer surgery. In particular, and using a probe described above, the combination of multiline laser excitation and parallel detection via a multichannel spectrometer enables classification of a 5×5 cm (or other) tissue region in under five (5) minutes, supporting real-time margin assessment during surgery. In a particular embodiment, the fiber bundle is driven be a plurality of continuous wave (CW) laser sources each emitting at a distinct wavelength, e.g., at 532, nm, 660 nm and 785 nm, optionally with a wavelength division multiplexer (WDM) to combine these wavelengths into a single output, and the multichannel spectrometer is optically coupled to the collection fibers and including the plurality of detector channels configured for parallel acquisition of Raman spectra from multiple spatial locations.

In another variant embodiment, outputs from the Raman spectroscopy and shear wave elastography are combined (co-registered) with other imaging techniques such as optical coherence tomography (OCT) and/or fluorescence-based contrast imaging through a real-time AI-enhanced image fusion algorithm. The results of this image fusion may be overlaid on functional or structural maps to identify and continuously localize suspicious tissue with high specificity. As previously described, this fused data may be transmitted to an HMD, microscope ocular, or monitor-based overlay to provide surgeons with a real-time guidance system for the probe. In this way, the projected display highlights regions of interest, optimal probe alignment trajectories, and ablation boundaries, enabling safe and targeted interventions. The probe may optionally be mounted on a robotic arm or stabilized via a handheld gimbal system to ensure consistent alignment with the target tissue. This minimizes user-induced variability and ensures accurate targeting, particularly when ablating microscopic margins or difficult-to-access tumor zones.

While in the preferred embodiment there are two detection modalities (Raman and SWE) and one mitigation/destruction modality (the ablation laser), this is not a limitation either. Generalizing, the multimodal intraoperative probe comprises one or more search modalities, and one or more destroy modalities, arranged coaxially within the handheld or robot-supported probe housing so as to target intraoperatively a same target area.

What is claimed is set forth below.

The invention claimed is:

1. An intraoperative surgical probe for detecting and treating cancerous tissue in real-time, comprising:
- a housing;
- a motion tracking unit that receives one or more inputs, and in response continually generates tracking data representing a displacement of a focal region of tissue, and a predicted motion of the focal region over a given time horizon;
- a first detection unit controllable to output a first output beam along a first axis, and in response receive first data;
- a second detection unit controllable to output a second output beam along a second axis, and in response receive second data;
- a treatment unit controllable to output a third output beam along a third axis
- wherein the first, second and third axes are co-aligned so as to selectively converge one or more of the first, second and third output beams on the focal region of tissue; and
- a control unit having a first portion, a second portion, and a third portion;
  - the first portion receiving and processing the tracking data to generate one or more output signals indicating that a residual motion of the focal region is less than a threshold;
  - the second portion responsive to a first output signal to activate the second detection unit in association with the first detection unit, to receive and analyze the first and the second data, generate respective first and second diagnostic outputs, and based on the first and second diagnostic outputs classify the tissue as normal or diseased; and
  - the third portion responsive to an indication from the second portion that the tissue is diseased together with receipt of a second output signal to arm the treatment unit to output the third output beam on the focal region of tissue.

2. The intraoperative surgical probe as described in claim 1, wherein the control unit includes a fourth portion, the fourth portion responsive to an activation of the treatment unit together with receipt of a third output signal to initiate a re-scan of the focal region of tissue.

3. The intraoperative surgical probe as described in claim 1, wherein the motion tracking unit comprises one or more sensors, wherein a sensor is one of: an ultrasound displacement sensor, an optical surface tracking sensor, an inertial measurement unit (IMU), an electromagnetic sensor, and a sensor responsive to one or more physiolic references.

4. The intraoperative surgical probe as described in claim 3, wherein the one or more physiolic references are one of: ECG-mid-diastole, and respiration.

5. The intraoperative surgical probe as described in claim 1, wherein the tracking data also includes a confidence level, and wherein an output signal of the one or more output signals is generated when the residual motion of the focal region is less than the threshold within the confidence level.

6. The intraoperative surgical probe as described in claim 1, wherein the first detection unit is a Shear Wave Elastography (SWE) unit, the first axis is an acoustic axis, the first output beam is an ultrasound beam, and the first data is data representing stiffness of the focal region of tissue.

7. The intraoperative surgical probe as described in claim 1, wherein the second detection unit is a Raman spectroscope, the second axis is an optical axis, the second output beam is scattered light, and the second data comprises Raman spectra.

8. The intraoperative surgical probe as described in claim 1, wherein the treatment unit is an ablation unit, the third axis is an optical axis, and the third output beam is coherent light.

9. The intraoperative surgical probe as described in claim 8, wherein the ablation unit destroys tissue and is one of: a cooled femtosecond pulsed laser, and a picosecond pulsed laser.

10. The intraoperative surgical probe as described in claim 1, wherein the treatment unit comprises a photodynamic therapy (PDT) subsystem configured to illuminate and thereby activate an administered photosensitizer at a therapeutically-effective wavelength to generate cytotoxic reactive species in the focal region.

11. The intraoperative surgical probe as described in claim 1, wherein the treatment unit comprises a photoimmunotherapy subsystem configured to illuminate and thereby activate an antibody-photosensitizer conjugate bound to target cells with near-infrared illumination to induce cell-selective phototoxicity in the focal region.

12. The intraoperative surgical probe as described in claim 1, wherein the given time horizon is in a range of 20-150 milliseconds.

13. The intraoperative surgical probe as described in claim 1, wherein the control unit second portion comprises a first machine learning model trained to classify the first data to produce the first diagnostic output, and a second machine learning model trained to classify the second data to produce the second diagnostic output.

14. The intraoperative surgical probe as described in claim 13, wherein the control unit second portion further comprises a third machine learning model trained to classify a fusion of first and second diagnostic outputs to produce an output prediction classifying the tissue as normal or diseased.

15. The intraoperative surgical probe as described in claim 5, wherein the confidence level is adjusted based on a prior diagnostic determination about the tissue, the prior diagnostic determination based on patient-specific data.

16. The intraoperative surgical probe as described in claim 1, further including a display supported in the housing on which an indication of the tissue as normal or diseased is rendered.

17. The intraoperative surgical probe as described in claim 2, wherein during the re-scan the first detection unit and the second detection unit are used to confirm absence of detectable residual disease.

18. The intraoperative surgical probe as described in claim 7, wherein the second detection unit is a wide-field Raman spectroscopy unit that provides multi-line Raman illumination and parallel detection of multiple Raman spectra.

19. The intraoperative surgical probe as described in claim 1, wherein the first detection unit operates according to a first modality, the second detection unit operates according to a second modality, and the treatment unit operates according to a third modality, wherein the first, second and third modalities differ from one another.

20. The intraoperative surgical probe as described in claim 1, wherein the housing is configured for one of: handheld support, and robotic support.

21. The intraoperative surgical probe as described in claim 1, wherein one of the first detection unit and the second detection unit are subjected to a compensation operation to cause the residual motion of the focal region to be less than the threshold.

22. The intraoperative surgical probe as described in claim 21, wherein the compensation operation is one of: beam steering, and micro-positioning.

* * * * *